(12) United States Patent
Wu

(10) Patent No.: US 11,839,356 B2
(45) Date of Patent: Dec. 12, 2023

(54) ENDOSCOPE DECONTAMINATION SHEATH

(71) Applicant: Chia-Ling Wu, New Taipei (TW)

(72) Inventor: Chia-Ming Wu, New Taipei (TW)

(73) Assignee: Chia-Ling Wu, New Taipei (TW)

(*) Notice: Subject to any disclaimer, the term of this patent is extended or adjusted under 35 U.S.C. 154(b) by 118 days.

(21) Appl. No.: 17/407,113

(22) Filed: Aug. 19, 2021

(65) Prior Publication Data

US 2023/0054775 A1 Feb. 23, 2023

(51) Int. Cl.
*A61B 1/00* (2006.01)

(52) U.S. Cl.
CPC ................. *A61B 1/00142* (2013.01)

(58) Field of Classification Search
CPC .......... A61B 1/00096; A61B 1/00101; A61B 1/00105; A61B 1/00135; A61B 1/00137; A61B 1/00142; A61B 2017/3458
See application file for complete search history.

(56) References Cited

U.S. PATENT DOCUMENTS

| | | | | |
|---|---|---|---|---|
| 2009/0112062 A1* | 4/2009 | Bakos | ................ | A61B 1/00087 600/114 |
| 2009/0253964 A1* | 10/2009 | Miyamoto | ......... | A61B 1/00091 600/157 |
| 2009/0264706 A1* | 10/2009 | Bala | ................... | A61B 1/00101 600/160 |
| 2013/0274554 A1* | 10/2013 | Sato | .................... | G02B 23/2423 600/121 |
| 2015/0196194 A1* | 7/2015 | Wu | ..................... | A61B 1/00142 600/125 |
| 2018/0078120 A1* | 3/2018 | Poll | ..................... | A61B 1/00101 |
| 2018/0084974 A1* | 3/2018 | Wake | ................. | A61B 1/00154 |
| 2019/0231175 A1* | 8/2019 | Dreyer | ..................... | A61B 1/07 |
| 2019/0246884 A1* | 8/2019 | Lu | ...................... | A61B 1/00105 |
| 2019/0274531 A1* | 9/2019 | Maiorano | .......... | A61B 1/00066 |
| 2020/0129049 A1* | 4/2020 | Panitz | .................. | A61B 5/0068 |
| 2020/0297193 A1* | 9/2020 | Takahashi | ............. | G02B 7/021 |
| 2021/0093160 A1* | 4/2021 | Eastwood | ........... | A61B 1/0055 |

* cited by examiner

*Primary Examiner* — Michael J Carey
*Assistant Examiner* — Stephen Floyd London
(74) *Attorney, Agent, or Firm* — Leong C. Lei

(57) ABSTRACT

An endoscope decontamination sheath includes a terminal section for seeing therethrough for an image and a sleeve section connected to the terminal section for receiving an endoscope to insert therein. The terminal section is of a tubular configuration. The terminal section has a front end to which a lens is mounted and a rear end in which an insertion groove is formed. The sleeve section is of an elongated tubular configuration having a front end fit into the insertion groove of the terminal section. In medical treatment of endoscopy or intubation, the endoscope is inserted into and sleeved with the sleeve section, and the endoscope sleeved with the decontamination sheath is inserted into an endotracheal tube. The matched arrangement between the lens and a lens of the endoscope helps prevent image deterioration and thus making images clearer. The decontamination sheath, after use, can be disposed of to prevent cross infection.

4 Claims, 6 Drawing Sheets

ENDOSCOPE DECONTAMINATION SHEATH

TECHNICAL FIELD OF THE INVENTION

The present invention relates to an endoscope decontamination sheath, and more particularly to an endoscope decontamination sheath that helps prevent cross inflection and cross contamination in endoscopy or intubation and that does not affect acquisition or capture of an image by a front-end lens of an endoscope.

DESCRIPTION OF THE PRIOR ART

An endoscope 1, which is commonly used in medical procedures, comprises a bougie 11, as shown in FIG. 6. The bougie 11 has a front end to which a tubular body 12 is mounted for receiving components, including a filter, a lens, and optical elements, to be arranged inside the tubular body 12, and a rear end to which an insertion piece 13 is mounted for insertion into and connection with a control circuit. To use, the endoscope 1 is inserted into the oral cavity of a patient and the control circuit is connected to a host device that includes a display. As being illuminated by the optical elements light, images of organs can be captured and acquired by the lens, and the images are transmitted to the control circuit at the rear end of the endoscope 1 to allow the image to be displayed on the display of the host device for observation.

The known endoscope 1 must be subjected to proper disinfection and decontamination after each use in order to prevent cross infection or cross contamination. This is labor- and time-consuming and it is impossible to achieve the purposes of completely eliminate cross infection or cross contamination. Consequently, a transparent sleeve 2 (such as plastic bag) is often fit over the endoscope 1 and after use, the used sleeve 2 is disposed of. This effectively prevents cross infection. However, the transparent sleeve 2 is formed by connecting multiple sheets together, so that the capture and acquisition of images by the front-end lens are affected when the endoscope 1 is fit therein, and further, the material that makes the sleeve 2 would cause deterioration of quality of images captured by the lens of the endoscope 1, and this would affect displaying of the image at the rear end, making it hard to effect observe minute details of symptoms. In view of such problems, the present invention aims to provide an endoscope decontamination sheath that helps prevent cross infection and cross contamination in endoscopy or intubation and that does not affect acquisition and capture of an image by a front-end lens of an endoscope.

SUMMARY OF THE INVENTION

The primary objective of the present invention is to provide an endoscope decontamination sheath that is fit over an endoscope in endoscopy or intubation and is disposed of after use so as to prevent cross infection and cross contamination and prevent deterioration of images for making images captured thereby clearer.

The endoscope decontamination sheath according to the present invention comprises a terminal section for seeing therethrough for an image; and a sleeve section connected to the terminal section for receiving an endoscope to insert therein, so that after medical treatment with endoscopy or intubation, the used decontamination sheath is disposable of to prevent cross infection and also to prevent image deterioration to thereby make an image captured with the endoscope clearer.

In the above endoscope decontamination sheath, the terminal section is a tubular body and the terminal section has a front end to which a lens is mounted. The terminal section is formed, in a rear end, with an insertion groove having a predetermined depth. The sleeve section is an elongated tubular body having a front end fit into and received in the insertion groove of the terminal section. In the medical treatment of endoscopy or intubation, the endoscope is inserted into and sleeved with the sleeve section, and the endoscope that is sleeved with the decontamination sheath is inserted into an endotracheal tube, wherein the matched arrangement between the lens and a lens of the endoscope helps prevent image deterioration and thus making a captured image clearer.

In the above endoscope decontamination sheath, the terminal section comprises an outer tubular body and an inner tubular body connected to the outer tubular body, wherein the outer tubular body is of a tubular configuration in the form of a cylindrical cap having a top end that is formed with a through hole for protrusion and exposure of the lens.

In the above endoscope decontamination sheath, the inner tubular body of the terminal section is provided with an upper stepped portion formed in an inside surface of an upper portion thereof and the lens is of an inverted T-shape, such that a protruding part of a lower portion of the lens is fit and retained in the stepped portion of the inner tubular body to allow a top of the lens exposed through the through hole formed in the top end of the outer tubular body.

In the above endoscope decontamination sheath, the inner tubular body pf the terminal section is provided with a lower stepped portion formed in an outside surface of a lower portion thereof, such that the insertion groove having the predetermined depth is defined between the inner tubular body and the outer tubular body in the lower portion.

DETAILED DESCRIPTION OF THE PREFERRED EMBODIMENT

Figure 1:
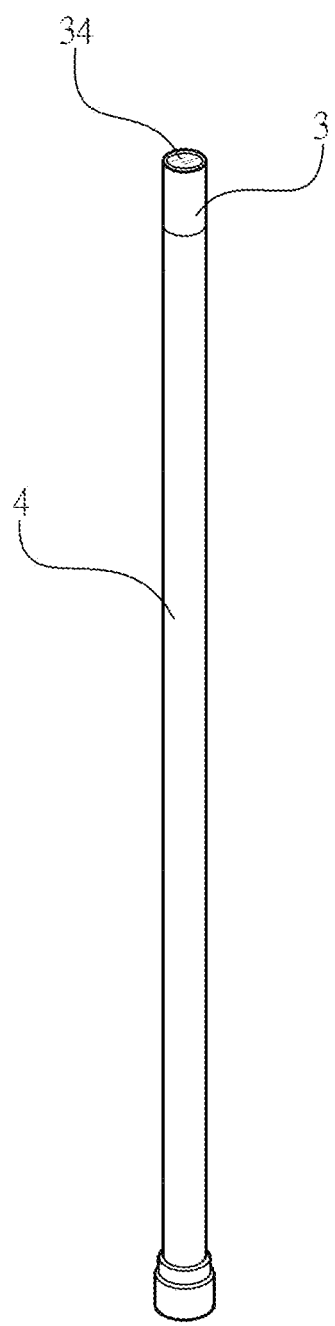
FIG. 1 is a perspective view of the present invention.
Figure 2:
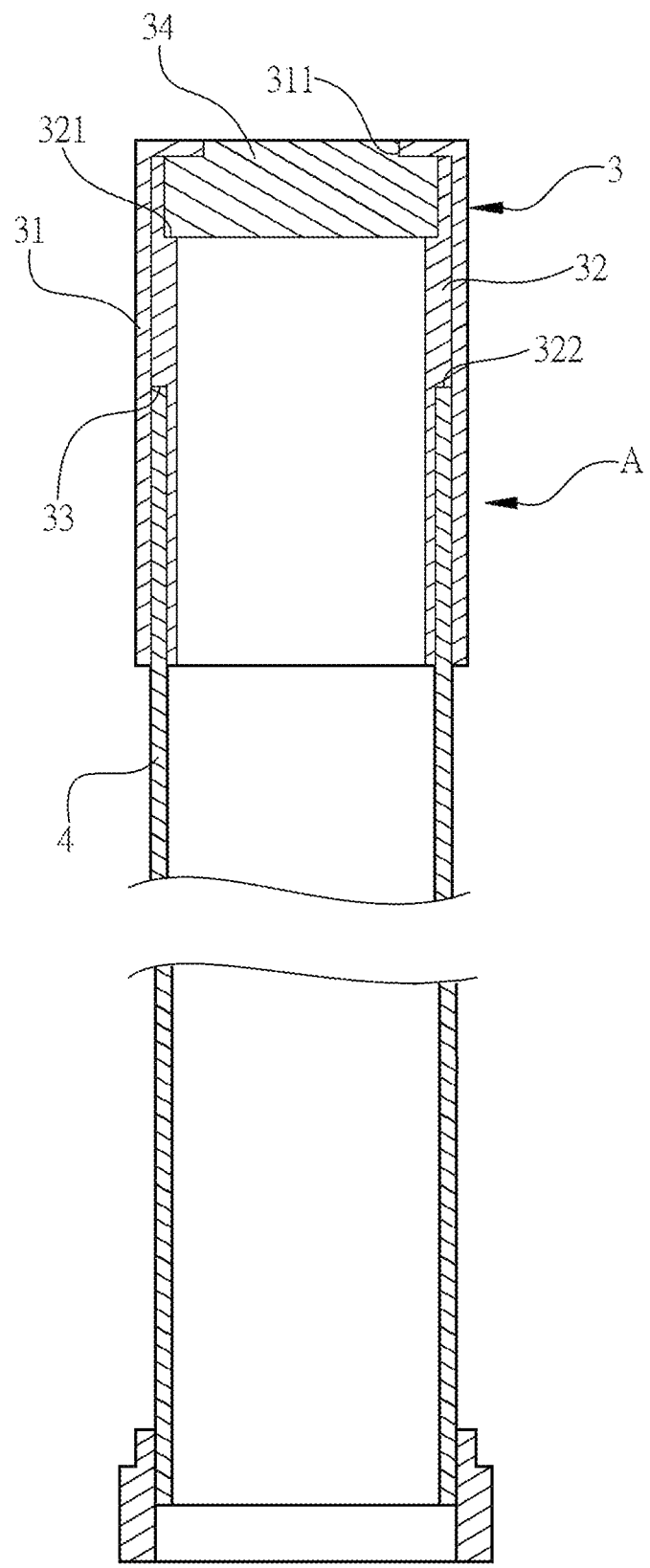
FIG. 2 is a cross-sectional view of the present invention.

Referring simultaneously to FIGS. 1 and 2, a perspective view and a cross-sectional view of the present invention are shown. As depicted in the drawings, the present invention comprises a terminal section 3 and a sleeve section 4 connected to the terminal section 3. In this structural arrangement, the terminal section 3 comprises an outer tubular body 31 and an inner tubular body 32 connected to the outer tubular body 31. The outer tubular body 31 is of a tubular configuration in the form of a cylindrical cap having a top end that is formed with a through hole 311. The inner tubular body 32 is of a tubular configuration in the form of a cylinder having an outer wall contacting and in tight engagement with an inner wall of the outer tubular body 31 and provided with an upper stepped portion 321 formed in an inside surface of an upper portion thereof and a lower stepped portion 322 formed in an outside surface of a lower portion, such that the inner tubular body 32 and the outer tubular body 31 define therebetween an insertion groove 33 in the lower portion. In the instant embodiment, the outer tubular body 31 and the inner tubular body 32 are formed of a stainless steel material.

A lens 34 is made in an inverted T-shape, so that a protruding part of a lower portion of the lens 34 is received into and retained in the stepped portion 321 of the inner tubular body 32 for positioning in such a way that a top portion of the lens 34 extending through and exposed through the through hole 311 formed in the top end of the outer tubular body 31. The lens 34 is preferably of a curved surface that corresponds to a curved surface of a lens of an endoscope.

The sleeve section 4 is made in the form of an elongated tube having an end inserted into and fit in the insertion groove 33 of the terminal section 3, with an opposite end forming an opening. In the instant embodiment, the sleeve section 4 is formed of a plastic material and has a top end fit into the insertion groove 33 of the terminal section 3 and applied with a bonding agent or adhesive for securely bonding.

The components as described above are assembled to form an endoscope decontamination sheath A. In medical treatment with endoscopy or intubation, an endoscope is inserted through the sleeve section 4 to be fit into and sleeved with the decontamination sheath A, and then, the endoscope that is sleeved with the decontamination sheath A is inserted into an oral cavity of a patient to allow an optical element at a front end of the endoscope to illuminate for enabling a lens to capture an image of an organ. In the capture of the image, the matched combination of the lens 34 and the lens of the endoscope makes it possible to prevent image deterioration and making the image so captured clearer. Further, after the medical treatment of endoscopy or intubation, the decontamination sheath A so used can be disposed of to avoid and prevent cross infection or cross contamination.

Figure 3:
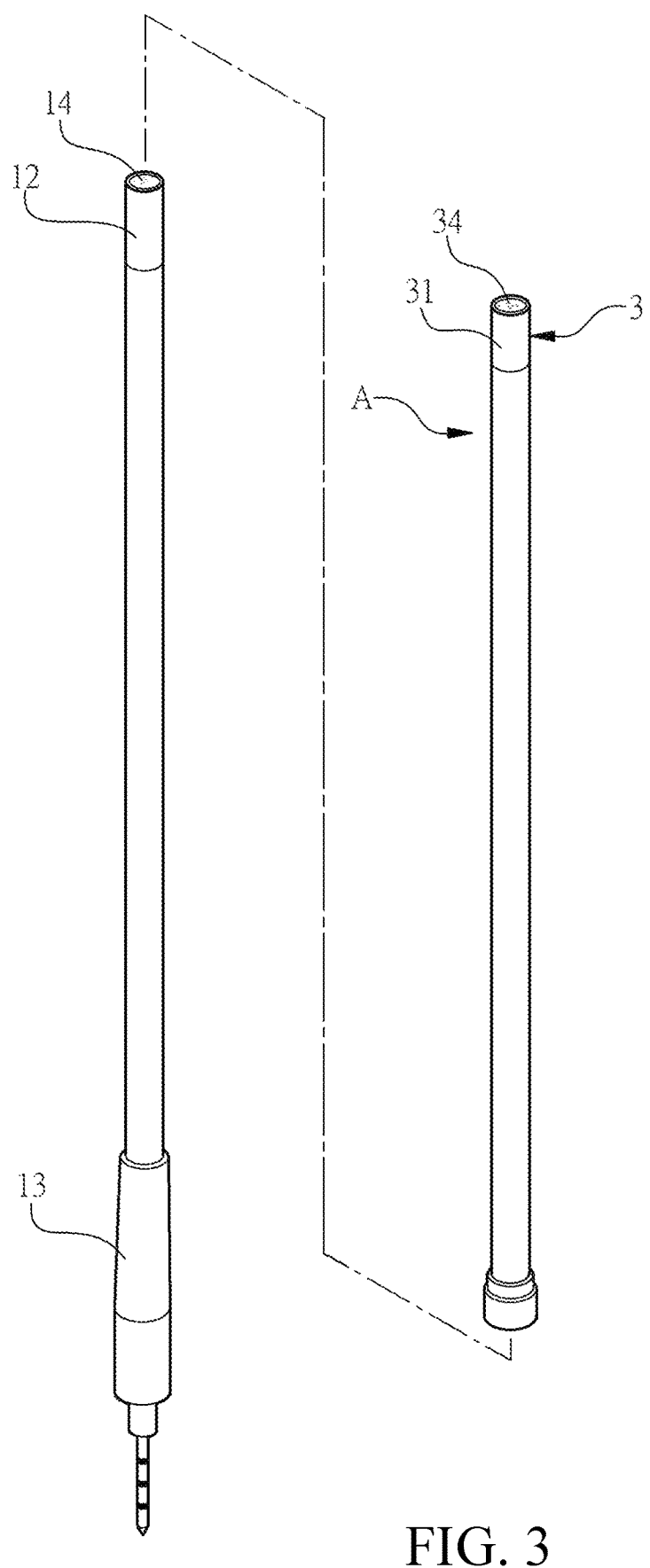
FIG. 3 is a perspective view showing a state of sleeving an endoscope according to the present invention.
Figure 4:
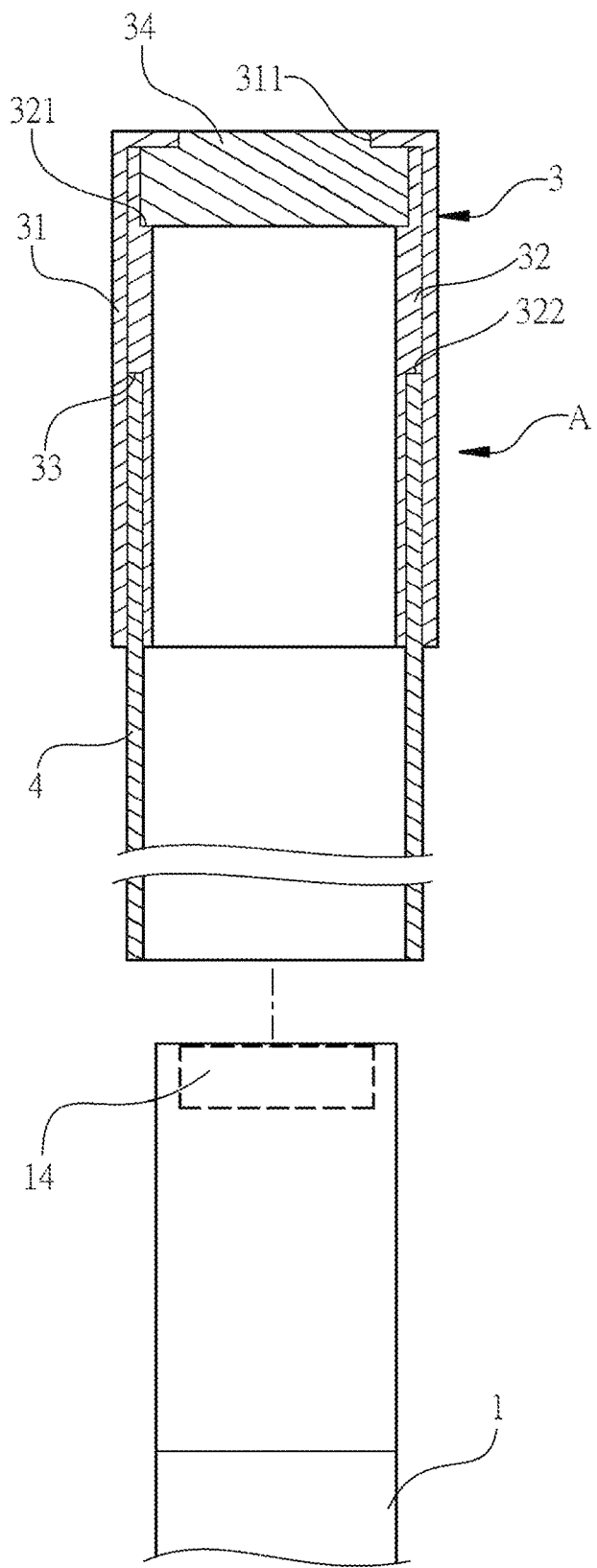
FIG. 4 is a cross-sectional view showing a state of sleeving an endoscope according to the present invention.
Figure 5:
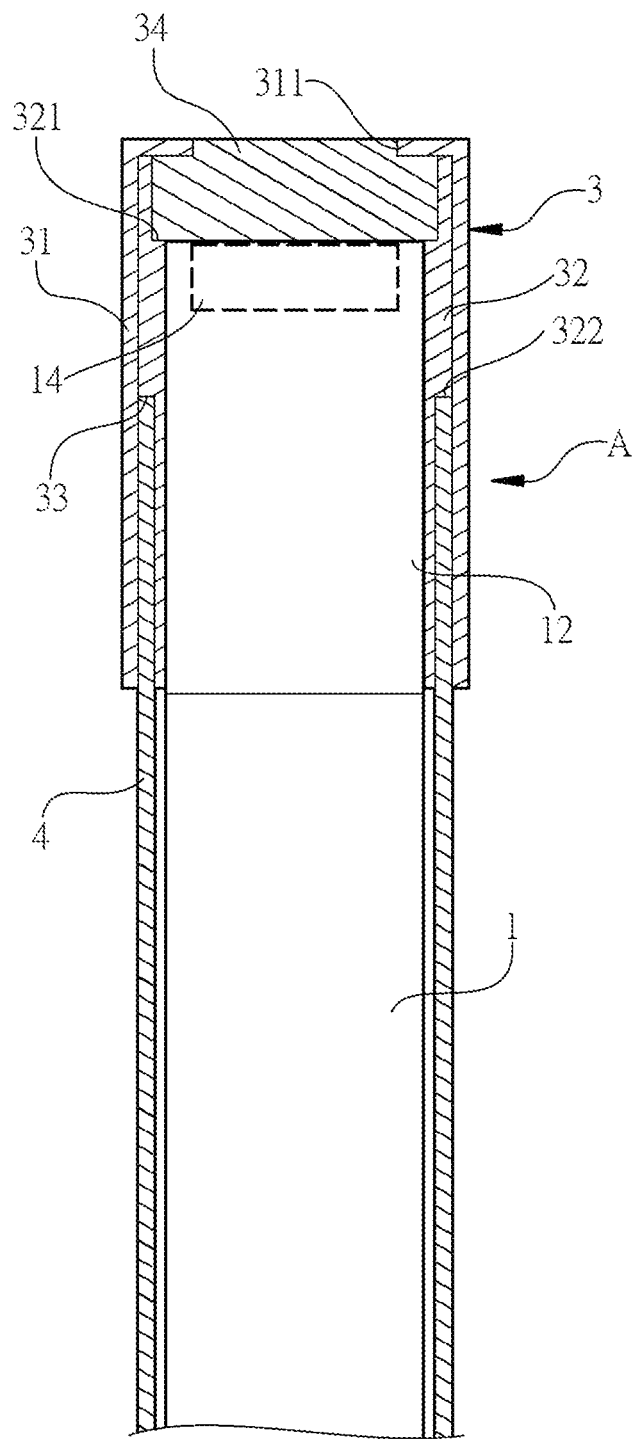
FIG. 5 is a cross-sectional view showing an endoscope sleeved in a decontamination sheath according to the present invention.
Figure 6:
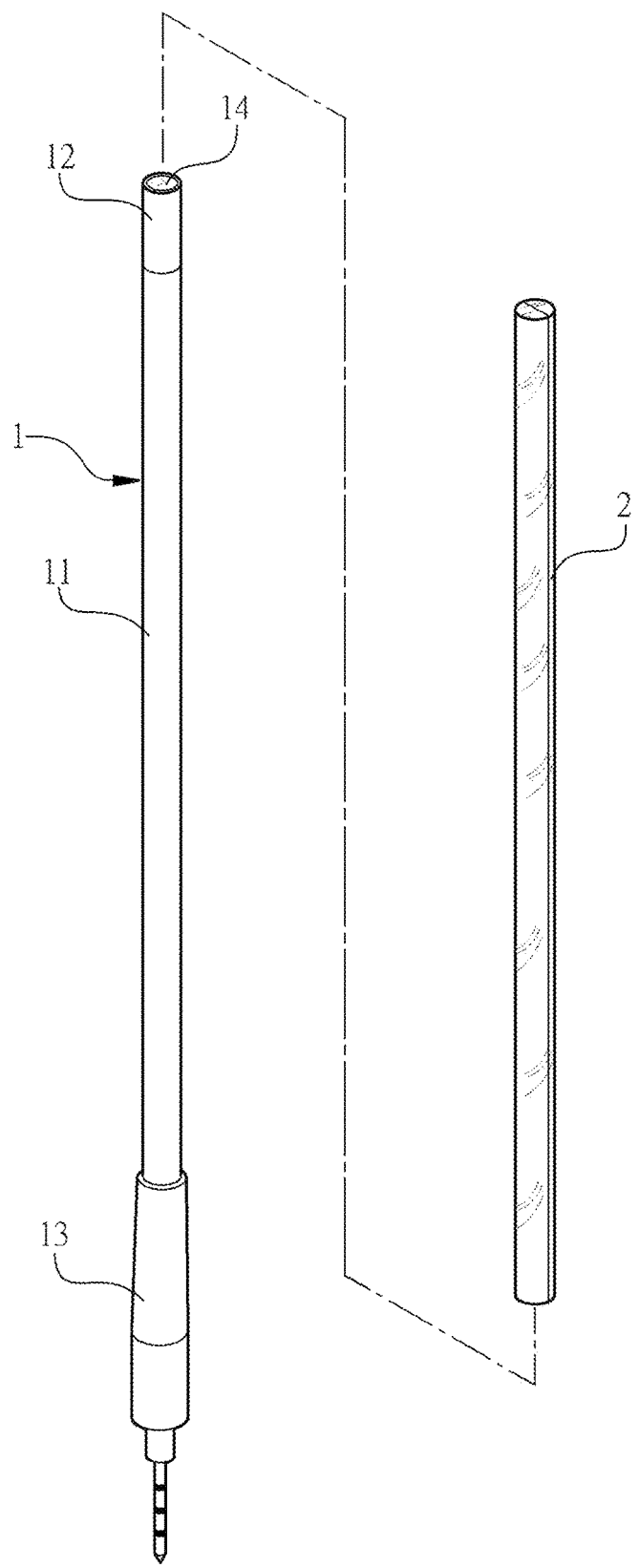
FIG. 6 is perspective vie showing a condition of fitting a known sleeve over a bougie of an endoscope.

Referring simultaneously to FIGS. 3 and 4, a perspective view showing a state of sleeving the endoscope according to the present invention and a cross-sectional view showing the state of sleeving the endoscope according to the present invention are provided. As shown in the drawings, to use the present invention, the endoscope 1 is inserted through the opening of the sleeve section 4 of the decontamination sheath A in order to have the endoscope 1 sleeved with and enclosed in the decontamination sheath A. After the endoscope 1 so inserted, the endoscope 1 can be inserted into the oral cavity of the patient for operation and the optical element at the front end of the endoscope 1 illuminates to enable the lens to capture an image of an organ. The image is transmitted to a control circuit that is connected to an insertion piece 13 at a rear end of the endoscope 1 to be displayed on a display of a host device for observation. After the medical treatment of endoscopy or intubation is finished, the decontamination sheath A so used can be disposed of for the purposes of preventing cross infection or cross contamination.

Referring to FIG. 4, a cross-sectional view showing the state of sleeving the endoscope according to the present invention is provided. As shown in the drawing, the endoscope 1 is so sleeved with and housed in the decontamination sheath A according to the present invention that the lens 14 of the endoscope 1 is in full surface contact engagement with and flat fitting with the lens 34 of the terminal section 3 of the decontamination sheath A in order to prevent undesired influence on image capture caused by light reflection. Since the curved surface or curvature of the lens 34 is identical to that of the lens 14, deterioration of image can be effectively avoided and further, due to incoming light being increased, a wide angle effect may be obtained for the image to therefore improve quality of medical treatment.

The embodiment provided above is just for illustration of a preferred way of practicing the present invention and is not intended for limiting the scope of the present invention. Minor modifications and alterations that do not deviate from the essence and gist of the present invention are considered falling within the scope of the present invention as defined in the appended claims.

In summary, the present invention provides a structure of an endoscope decontamination sheath that includes a lens having a curved surface or curvature corresponding to a lens of an endoscope and a terminal section formed with an insertion groove for collaborative combination with a sleeve section fit into and connectable to the terminal section. Such a structure allows an endoscope to be inserted therein and enclosed thereby in medical treatment with endoscopy or intubation and also allows for disposal of after used to prevent cross infection or cross contamination and also to prevent deterioration of image for making an image captured clearer to thereby improve quality of medical treatment.

I claim:

1. An endoscope decontamination sheath, comprising a terminal section; and
a sleeve section connected to the terminal section and adapted to receive an endoscope therein,
wherein the terminal section has a front end to which a lens is mounted and a rear end that is formed with an insertion groove having a predetermined depth;
wherein the sleeve section is an elongated tubular body having a front end fit into and received in the insertion groove of the terminal section;
wherein the terminal section comprises an outer tubular body and an inner tubular body connected to the outer tubular body, wherein the outer tubular body is of a tubular configuration in the form of a cylindrical cap having a top end that is formed with a through hole; and the inner tubular body is of a tubular configuration in the form of a cylinder having an outer wall in contact engagement with an inner wall of the outer tubular body, the cylinder of the inner tubular body having an upper end facing the top end of the cylindrical cap of the outer tubular body, an upper stepped portion being formed in an inside surface of the upper end of the cylinder of the inner tubular body and spaced from the top end of the cylindrical cap of the outer tubular body;
wherein a circumferential portion of the lens is interposed between the upper stepped portion of the cylinder of the inner tubular body and the top end of the cylindrical cap of the outer tubular body, and a central portion of the lens is partly received in the through hole of the top end of the cylindrical cap of the outer tubular body.

2. The endoscope decontamination sheath according to claim 1, wherein the inner tubular body is provided with a lower stepped portion formed in an outside surface of a lower portion, such that the inner tubular body and the outer tubular body define the insertion groove therebetween.

3. The endoscope decontamination sheath according to claim 1, wherein the outer tubular body and the inner tubular body are each formed of a stainless steel material.

4. The endoscope decontamination sheath according to claim 1, wherein the sleeve section is formed of a plastic material.

\* \* \* \* \*